US009031631B2

(12) United States Patent
Tong et al.

(10) Patent No.: US 9,031,631 B2
(45) Date of Patent: May 12, 2015

(54) BRAIN BIOFEEDBACK DEVICE WITH RADIALLY ADJUSTABLE ELECTRODES

(71) Applicant: The Hong Kong Polytechnic University, Hong Kong (HK)

(72) Inventors: Kai Yu Tong, Hong Kong (HK); Bun Yu, Hong Kong (HK); Peter Man Kit Pang, Hong Kong (HK); Newmen Sze Kit Ho, Hong Kong (HK); Xiaoling Hu, Hong Kong (HK); Robert Wai Man Tam, Hong Kong (HK); Shu To Ng, Hong Kong (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 137 days.

(21) Appl. No.: 13/754,919

(22) Filed: Jan. 31, 2013

(65) Prior Publication Data

US 2014/0213874 A1   Jul. 31, 2014

(51) Int. Cl.
*A61B 5/0478* (2006.01)
*A61B 5/00* (2006.01)

(52) U.S. Cl.
CPC ............. *A61B 5/0478* (2013.01); *A61B 5/6803* (2013.01)

(58) Field of Classification Search
CPC .................................................... A61B 5/0478
USPC .......................................... 600/383, 544, 545
See application file for complete search history.

(56) References Cited

U.S. PATENT DOCUMENTS 3,623,477 A * 11/1971 Trent ............................ 600/383
4,967,038 A * 10/1990 Gevins et al. ................. 600/383

5,357,957 A    10/1994 Itil et al.
5,479,934 A *  1/1996 Imran .......................... 600/544
5,891,028 A    4/1999 Lundbaeck
6,154,669 A    11/2000 Hunter et al.
6,175,753 B1   1/2001 Menkes et al.
6,201,982 B1   3/2001 Menkes et al.

(Continued)

FOREIGN PATENT DOCUMENTS

CN    2258747 Y    8/1997
CN    2902190 Y    5/2007

(Continued)

OTHER PUBLICATIONS

European Search report of 14152680.6 issued on May 12, 2014.

(Continued)

*Primary Examiner* — Lee S Cohen
(74) *Attorney, Agent, or Firm* — Ella Cheong Hong Kong; Sam T. Yip

(57) ABSTRACT

A head-mountable EEG electrode-containing device is provided based on radially adjustable electrodes to fit the wearer's unique head size and shape. The head-mountable device with an electrode array positioned therein includes multiple head-mountable device sections that are interconnected by mechanical fasteners to facilitate sizing and positioning of the head-mountable device. An array of resilient sleeves is positioned within each head-mountable device section. Each resilient sleeve houses an individual electrode and is deformable for self-orienting. The deformation of the sleeve is such that a central axis passing through the individual electrode housed within the resilient sleeve is maintained in a position approximately normal to a plane tangential to a scalp portion positioned beneath that electrode.

7 Claims, 16 Drawing Sheets

(56) References Cited

U.S. PATENT DOCUMENTS

| | | |
|---|---|---|
| 6,381,481 B1 | 4/2002 | Levendowski et al. |
| 6,574,513 B1 | 6/2003 | Collura et al. |
| 6,640,122 B2 | 10/2003 | Manoli et al. |
| 2001/0044573 A1 | 11/2001 | Manoli et al. |
| 2002/0029005 A1 | 3/2002 | Levendowski et al. |
| 2002/0183605 A1 | 12/2002 | Devlin et al. |
| 2002/0188216 A1 | 12/2002 | Kayyali et al. |
| 2005/0059899 A1 | 3/2005 | Merilainen et al. |
| 2005/0165323 A1 | 7/2005 | Montgomery et al. |
| 2006/0161058 A1 | 7/2006 | Ives et al. |
| 2007/0093706 A1 | 4/2007 | Gevins et al. |
| 2007/0225585 A1 | 9/2007 | Washbon |
| 2008/0154112 A1 | 6/2008 | Murphy et al. |
| 2009/0171181 A1* | 7/2009 | Kumada et al. .............. 600/383 |
| 2009/0234242 A1 | 9/2009 | Svojanovsky |
| 2010/0036275 A1 | 2/2010 | Alkire |
| 2010/0059274 A1 | 3/2010 | Ives et al. |
| 2010/0268096 A1 | 10/2010 | Berka et al. |
| 2011/0004089 A1 | 1/2011 | Chou |
| 2011/0015503 A1 | 1/2011 | Joffe et al. |
| 2011/0066020 A1 | 3/2011 | Svojanovsky |
| 2011/0098593 A1 | 4/2011 | Low |
| 2011/0282231 A1 | 11/2011 | Pradeep et al. |
| 2011/0282232 A1 | 11/2011 | Pradeep et al. |
| 2012/0036005 A1 | 2/2012 | Pradeep et al. |
| 2012/0071781 A1 | 3/2012 | Fadem |
| 2012/0108998 A1 | 5/2012 | Molnar et al. |
| 2012/0143020 A1 | 6/2012 | Bordoley |
| 2012/0172682 A1 | 7/2012 | Linderman et al. |
| 2012/0203130 A1 | 8/2012 | Bernhard |
| 2012/0232372 A1 | 9/2012 | Wilson et al. |

FOREIGN PATENT DOCUMENTS

| | | |
|---|---|---|
| CN | 201139565 Y | 10/2008 |
| CN | 202161317 U | 3/2012 |
| DE | 102010056099 A1 | 6/2012 |
| EP | 2474263 A1 | 7/2012 |
| TW | 200934444 A | 8/2009 |
| TW | 201204322 A | 2/2012 |
| TW | M428785 U | 5/2012 |
| WO | 0101856 A1 | 1/2001 |
| WO | 0101857 A1 | 1/2001 |
| WO | 02053027 A1 | 7/2002 |
| WO | 03005897 A2 | 1/2003 |
| WO | 2005094674 A1 | 10/2005 |
| WO | 2007059248 A2 | 5/2007 |
| WO | 2008109694 A1 | 9/2008 |
| WO | 2008115189 A2 | 9/2008 |
| WO | 2008119031 A1 | 10/2008 |
| WO | 2009055455 A2 | 4/2009 |
| WO | 2009065006 A2 | 5/2009 |
| WO | 2009087486 A2 | 7/2009 |
| WO | 2010124317 A1 | 11/2010 |
| WO | 2010129026 A2 | 11/2010 |
| WO | 2011112652 A1 | 9/2011 |
| WO | 2011123059 A1 | 10/2011 |
| WO | 2011123072 A1 | 10/2011 |
| WO | 2011140303 A1 | 11/2011 |
| WO | 2012036639 A1 | 3/2012 |
| WO | 2012097872 A1 | 7/2012 |
| WO | 2012105493 A1 | 8/2012 |
| WO | 2012140629 A1 | 10/2012 |
| WO | 2012140719 A1 | 10/2012 |
| WO | 2012150528 A1 | 11/2012 |

OTHER PUBLICATIONS

R. Ball, C. Shu, P. C. Xi, M. Rioux, Y. Luximon, and J. Molenbroek, "A comparison between Chinese and Caucasian head shapes," Applied Ergonomics, vol. 41, pp. 832-839, 2010.

Z. Zhuang, S. Benson, D. Viscusi. "Digital 3-D headforms with facial features representative of the current U.S. work force," Ergonomics; 53: 661-71, 2010.

China National Institute of Standardization. (1998) CNIS GB/T2428:1998. Head-face dimensions of adults by Xiao H, Hua DH, Yang TX, Zhang ZB, Bi GX, Liu JM. Beijing, China: General Administration of Quality Supervision, Inspection and Quarantine of the People's Republic of China.

China National Institute of Standardization. (1981) CNIS GB2428-81. Head styles of adults by Beijing Institute of Labor Protection. Beijing, China: General Administration of Quality Supervision, Inspection and Quarantine of the People's Republic of China.

Y. Yu, S. Benson, W. Cheng, J. Hsiao, Y. Liu, Z. Zhuang and W. Chen. "Digital 3-D Headforms Representative of Chinese Workers" Ann. Occup. Hyg., pp. 1-10, 2011.

Ball, R.M. (2011) "SizeChina: A 3D Anthropometric Survey of the Chinese Head".

* cited by examiner

BRAIN BIOFEEDBACK DEVICE WITH RADIALLY ADJUSTABLE ELECTRODES

FIELD OF THE INVENTION

The invention relates to an EEG brain biofeedback device for rehabilitation, training or entertainment and, more particularly, to a brain biofeedback device having self-orienting, radially-adjustable EEG electrodes.

BACKGROUND OF THE INVENTION

Stroke is a cerebrovascular accident with high disability and mortality rates. One of the main factors affecting the independence of stroke survivors is hand function, which is closely related to daily activities, such as feeding and self-cleaning. Neuro-rehabilitation following a stroke or other cerebrovascular event is a major future challenge as populations age and have increasing longevity.

Electroencephalography (EEG) is a technique for measuring bioelectrical signals generated by the cerebral cortex of a brain. The signals are directly related to voluntary motor contributions from the central nervous system (e.g., EEG motor imagery, the thinking and planning of a physical task). EEG signals are more directly related to the voluntary contribution with stronger signals from a patient in the early post-stroke stage. Currently the types of EEG systems that can measure these signals are non-portable, that is, they are sufficiently large as to restrict their use to a research laboratory environment. The measurement system requires a lengthy period to prepare and correctly position all the EEG electrodes. Further, without visual indicators, correct electrode placement is difficult to verify and typically must be performed by skilled technicians.

Various devices have been used in an attempt to correctly position and hold EEG electrodes adjacent to a patient's scalp. For example, caps are used to position the EEG electrodes. Such electrode caps facilitate positioning of EEG electrodes by technicians within a short period of time (e.g., about 5 minutes). Following electrode positioning, conductive gel is injected to reduce the scalp-electrode impedance and thereby record strong EEG signals.

However, conventional attempts to position EEG electrodes using various headgear are insufficient because they do not appropriately account for variations among head sizes and shapes in the patient population. Typically, conventional approaches use several specific sizes in order to approximate various head sizes along with elastic materials to roughly elongate a cap to more closely fit different head shapes. However, conventional electrode caps are based on approximating the upper head as having a hemispherical shape. Since the human head does not have a hemispherical shape, an equal elongated head size approximation method causes error in the electrode positioning.

Thus there is a need in the art for an improved EEG electrode positioning device, particularly a positioning device that is lightweight with sufficient resilient properties to ensure proper electrode positioning on a variety of head sizes and shapes. There is a further need in the art for visual indication that the electrodes are correctly positioned and that the electrode-scalp impedance is within an acceptable range for EEG signal measurement. Such a device could facilitate a portable brain-training system with minimal set-up time that could be used in clinical and residential settings.

SUMMARY OF THE INVENTION

The present invention presents a novel head-mountable EEG electrode-containing device based on radially adjustable electrodes to fit the wearer's unique head size and shape rather than merely laterally elongating the space between electrodes as in conventional electrode caps.

A head-mountable device with an electrode array positioned therein includes multiple head-mountable device sections that are interconnected by mechanical fasteners to facilitate sizing and positioning of the head-mountable device. An array of resilient sleeves is positioned within each head-mountable device section. Each resilient sleeve houses an individual electrode and is deformable. The deformation of the sleeve is such that a central axis passing through the individual electrode housed within the resilient sleeve is maintained in a position approximately normal to a plane tangential to a scalp portion positioned beneath that electrode.

BRIEF DESCRIPTION OF THE DRAWINGS

FIG. 7B shows the self-orienting properties of the electrode with a central axis passing through the electrode maintained in a position approximately normal to a plane tangential to the portion of the scalp positioned beneath the electrode.

DETAILED DESCRIPTION OF THE INVENTION

Figure 2:
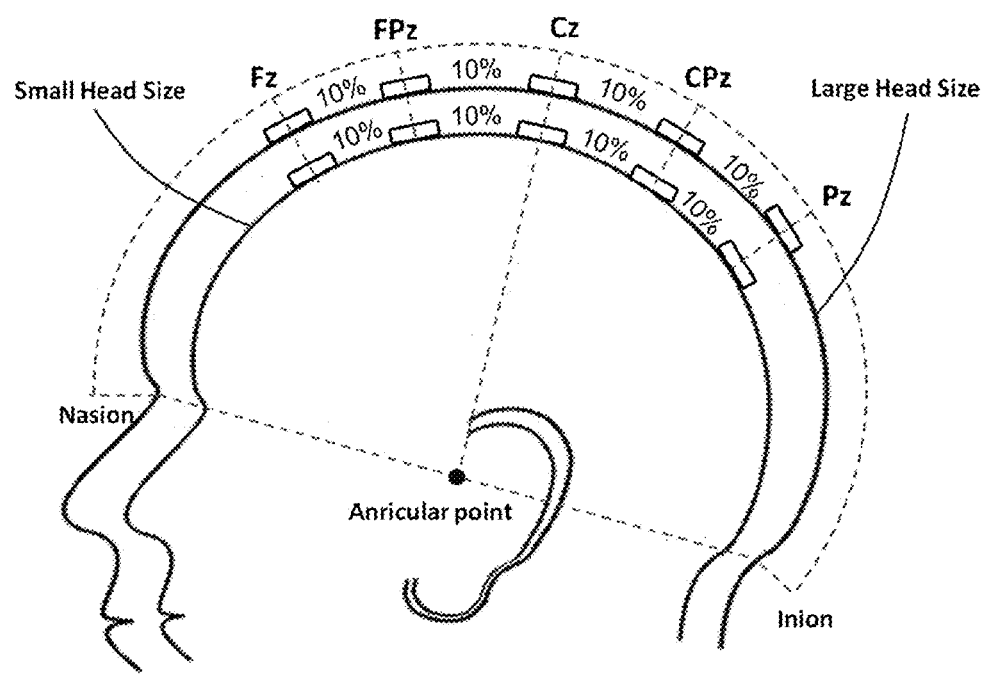
FIG. 2 schematically depicts expansion of a head dimension in a radial direction based on measurements of human populations.

Turning to the drawings in detail, FIG. 2 depicts an extension of a head size in a radial direction obtained by comparing standard head shapes and sizes (see references 1-6) according to the present invention. Using these measurements and extensions, the present invention creates a new design for a head-mountable electrode array device. The device relies on radially adjustable electrodes that fit an individual head size in contrast to conventional elastic caps that laterally elongate the space between the electrodes.

Figure 3A:
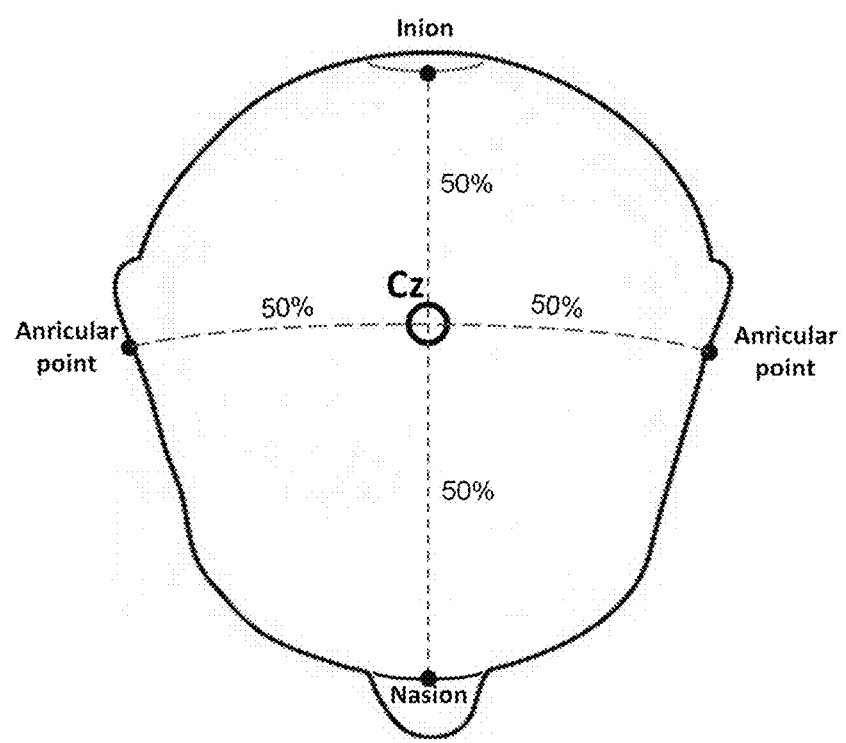
FIGS. 3A and 3B depict top and side views of positioning points for the head-mountable device electrode array of the present invention.
Figure 3B:
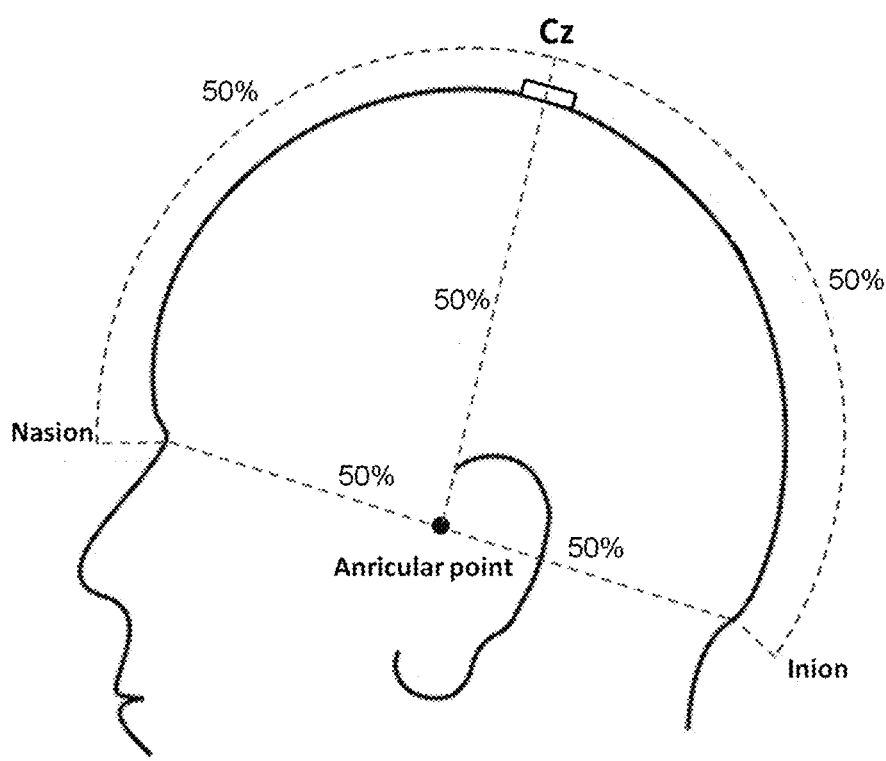

Turing to FIG. 3, the head-mountable device is attached on the wearer's head using the precise orientation and position with reference to the nasion and inion, and also the ear auricular points to find the vertex point (Cz), which is the central point between nasion and inion and also the central point between left and right auricular points. The device is also aligned with the central line, which runs along the nasion and inion.

Figure 1:
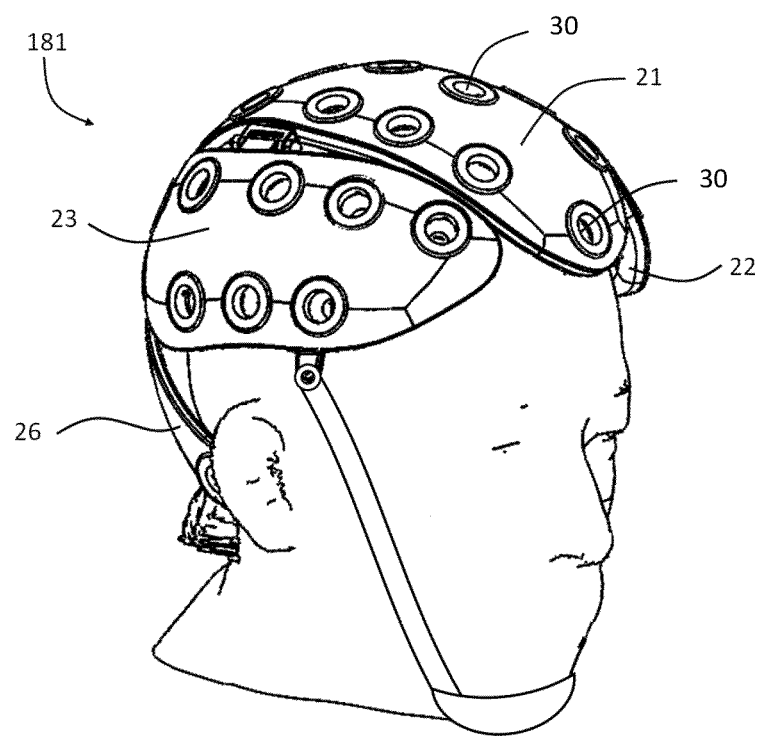
FIG. 1 is a perspective view of a brain training device consisted of EEG headset module in accordance with a preferred embodiment of the present invention as worn.

Based on the measurements and positions of FIGS. 2 and 3, FIG. 1 depicts a head-mountable device 181 that can measure bioelectrical signals generated by a cerebral cortex of a brain configured such that individual electrodes are radially adjustable for individual variations in head size and shape. The device of FIG. 1 is optionally part of a system used for brain training and rehabilitation.

Figure 4A:
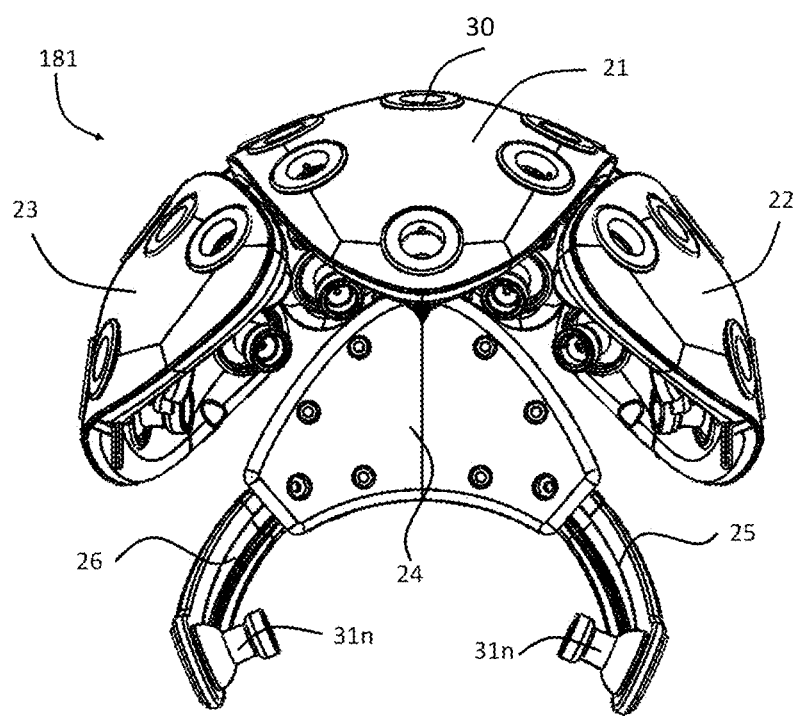
FIGS. 4A and 4B are, respectively, front and side views of the EEG headset module of the device of FIG. 1.
Figure 4B:
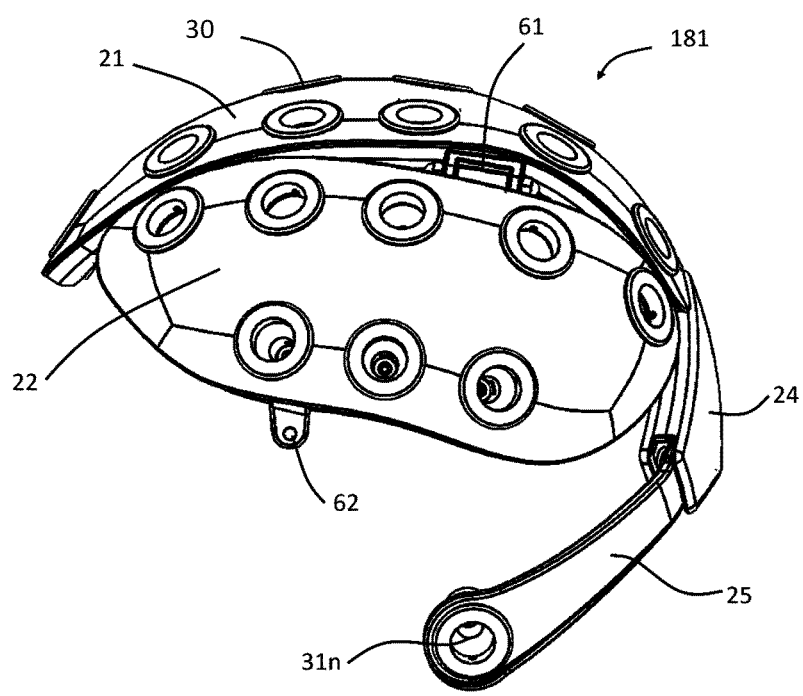
Figure 5:
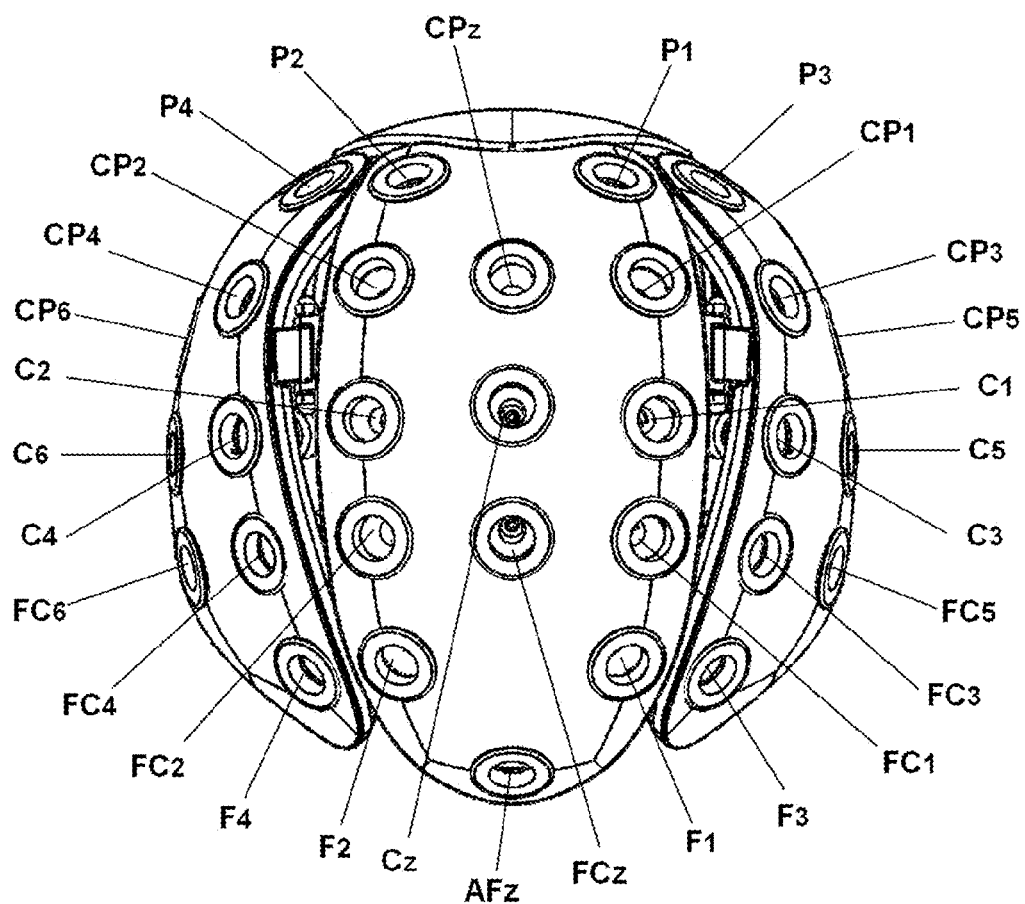
FIG. 5 is a top view of the EEG headset module of the device of FIG. 1 indicating the EEG electrode positions which covered the central, frontal and parietal regions of the brain activity based on the EEG electrode location from the International 10/20 system for a 64 channel EEG.

Referring to FIGS. 4 and 5, the EEG head-mountable device 181 includes EEG electrode positions 30 covering the central, frontal and parietal regions of the skull of the head according to the international 10/20 system. The numeral 30 is used to indicate the overall electrode structure while the bioelectrical signal sensing portion (the actual electrical portion of the electrode) is indicated by reference numeral 32 (see FIG. 6). The numeral 38 is used to indicate the outer shell of the head-mountable device 181. The head-mountable device 181 comprises central device segment 21, left device segment 22, right device segment 23 and auxiliary device segment 24. The auxiliary segment 24 includes left and right back ear reference electrodes 31n. Each of the EEG electrodes 30 is affixed to a predetermined electrode position in the EEG head-mountable device. An electrode is placed with spacing of 20% of the nasion-inion distance and 20% of the ear auricular distance for the vertical and horizontal line respectively according to the standard 10/20 system. For a 64-channel EEG, the vertical distance between electrodes is reduced by half and becomes 10% of the nasion-inion distance and the horizontal distance becomes 10% of the ear auricular distance.

Figure 6:
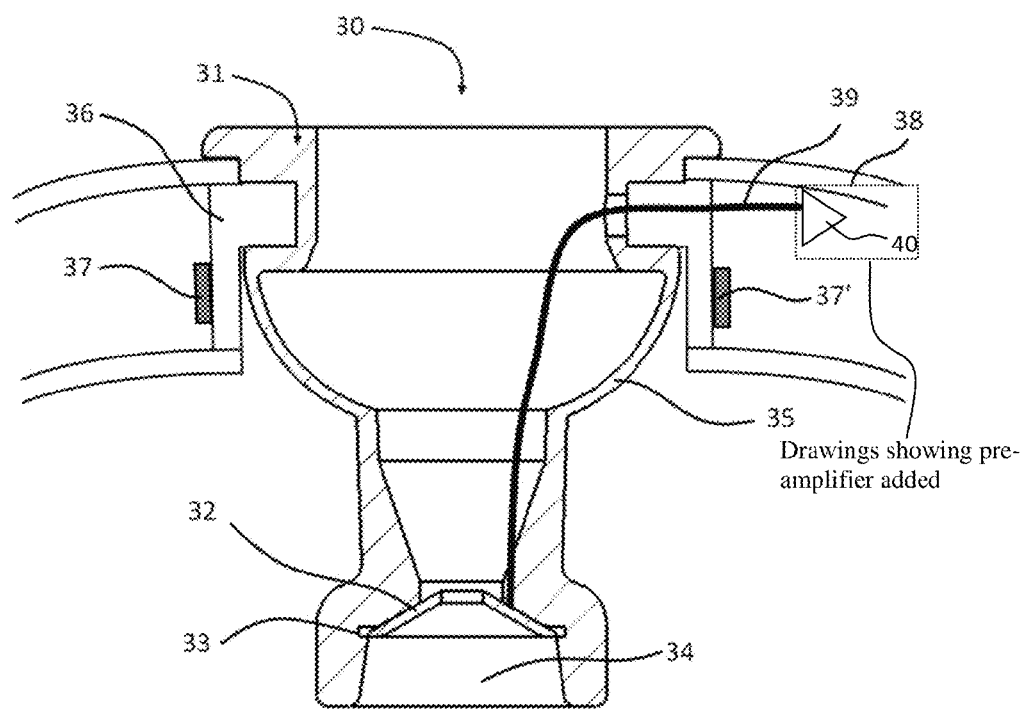
FIG. 6 is a cross-sectional view illustrating details of a self-orienting EEG electrode attached inside the headset module of the device of FIG. 1.
Figure 7A:
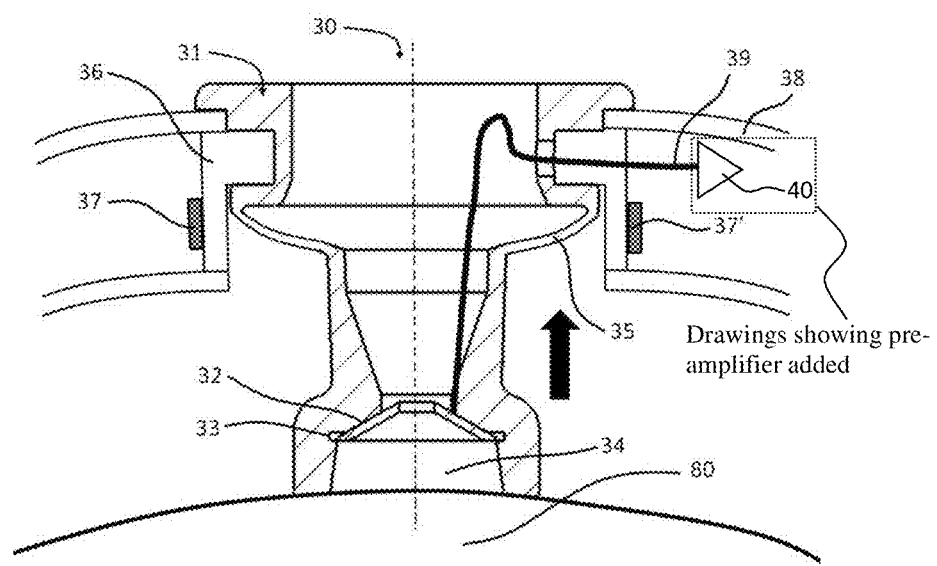
FIGS. 7A and 7B are cross-sectional views of a self-orienting EEG electrode of FIG. 6 in contact with the skin surface with a certain distance and angle that the electrode can be placed on the various size and shape of the head.
Figure 7B:
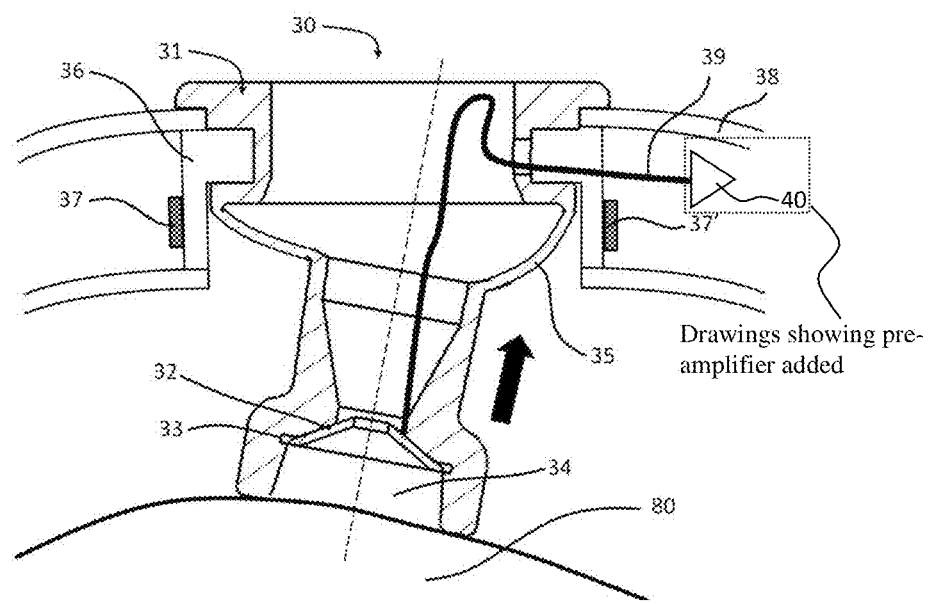

FIG. 6 is a cross-sectional view of an electrode 30. The bioelectrical sensing portion 32 is positioned within a resilient electrode sleeve 31. The resilient electrode sleeve 31 is an integrally-formed structure that includes semicircular damper portion 35. This configuration allows the resilient sleeve 31 to be compressed within a certain distance to change its orientation to adapt to various head sizes and shapes as shown in FIGS. 7A and 7B. As seen in FIGS. 7A and 7B, the electrode 32 is mounted within resilient sleeve 31 such that when the resilient sleeve with damper portion 35 is deformed, a central axis passing through electrode 32 is maintained in a position approximately normal to a plane tangential to a scalp portion positioned beneath the electrode for self-orienting.

The EEG electrode 32 is positioned within the sleeve having distal ends/legs embedded in the annular groove 33 of the resilient sleeve 31. Embedding the EEG sensing electrode 32 inside the self-orienting electrode sleeve 31 and fixing the orientation of cable 39 minimizes the possibility of EEG electrode dislocation.

At the portion of the resilient sleeve 31 directly adjacent to a patient's scalp, a cavity 34 is formed. This cavity is typically filled with a conductive gel to provide contact between the scalp and the electrode. Alternatively, a deformable conductive material can fill cavity 34 for provide the needed skin-electrode impedance. The annular edge of the resilient sleeve 31 can also be placed on the head comfortably and minimize the leakage from the electrode during head movement. The conductive gel can reduce the skin-electrode impedance between the EEG electrode 32 and scalp 80 of the head. This design can reduce the skin-electrode impedance to enhance the EEG signal quality.

Figure 8:
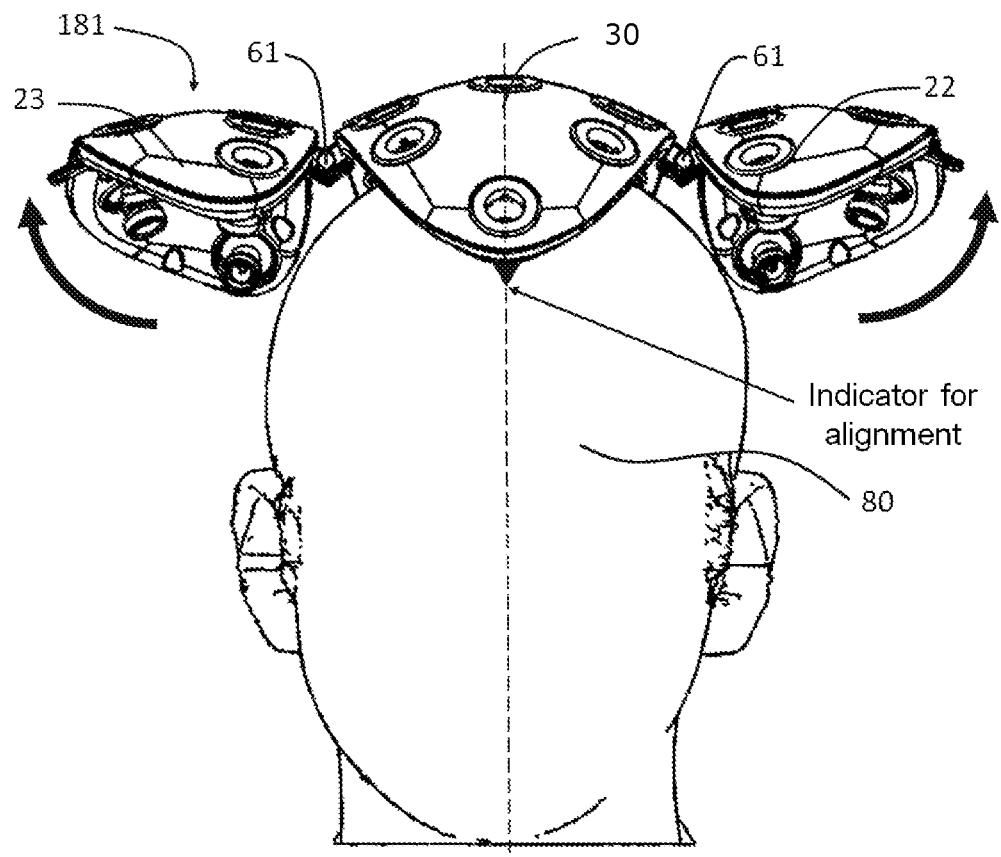
FIG. 8 is a front view of the EEG headset module of the device of FIG. 1 when both left and right segments of the EEG headset module are bent upward for placing the device on the head or removing the device from the head.
Figure 9:
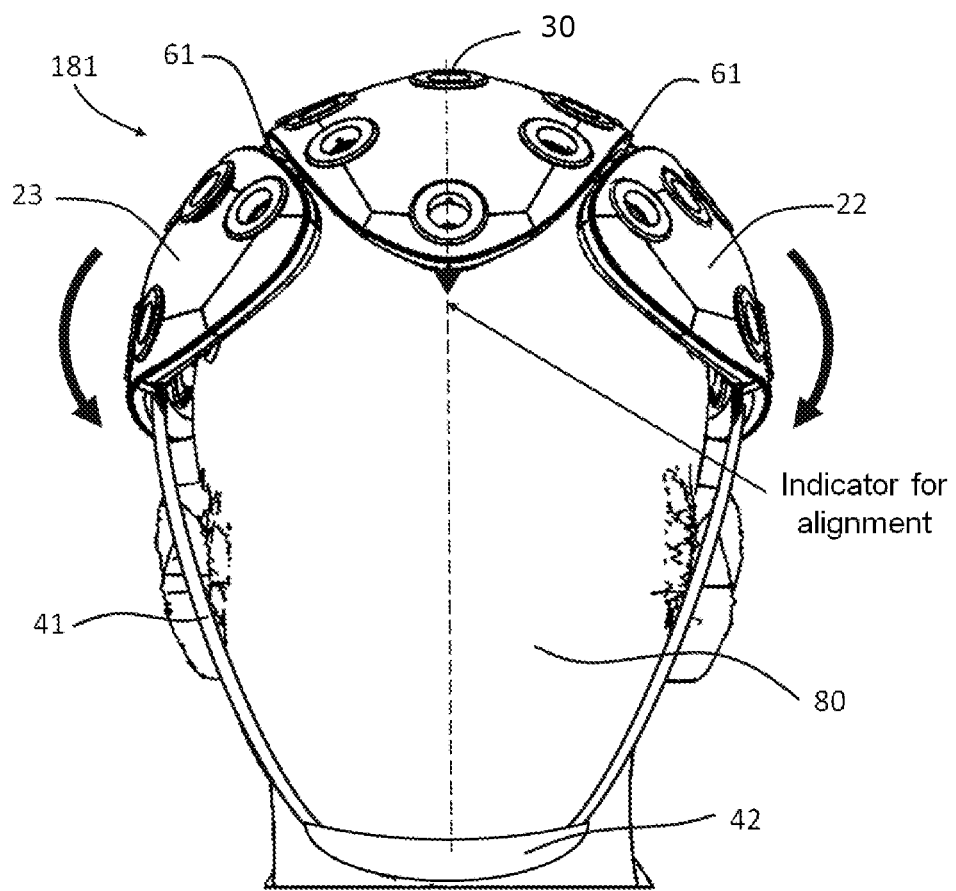
FIG. 9 is a front view of the EEG headset module of the device of FIG. 1 when both left and right segments of the EEG headset module are attached on the head surface.

Referring to FIGS. 8 and 9, the left segment 22 and right segment 23 of the EEG head-mountable device 181 can be bent upward and downward by mechanical fasteners (optionally formed by a hinge joint 61) during application and removal of device 181. Advantageously, the relative movement of the sections to one another avoids deforming the electrode at the left segment 22 and right segment 23 of the EEG head-mountable device during application of the device. However, the electrode sleeve 31 will deform radially and self-orient at the desired electrode position on the patient's head (that is, with the central axis of the electrode substantially perpendicular to a line tangent to the scalp beneath the electrode).

Figure 10A:
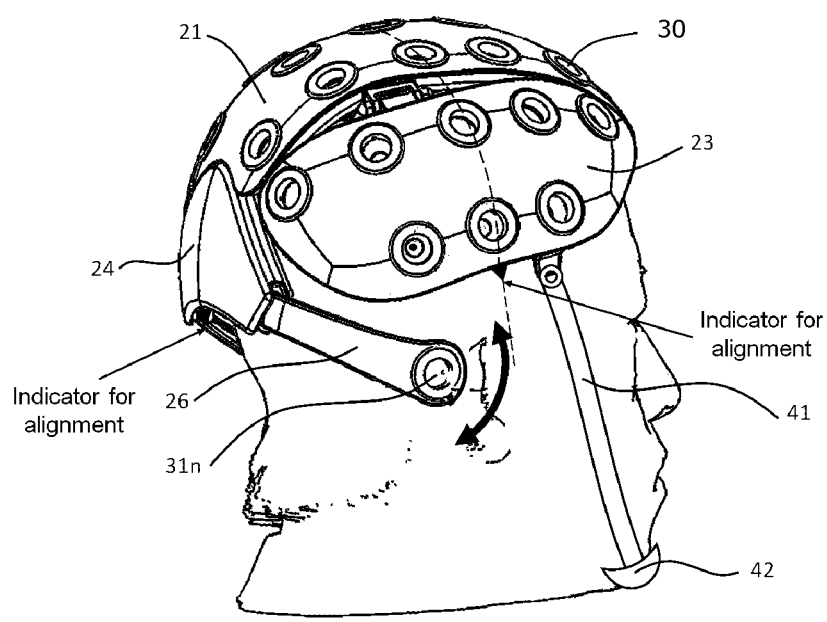
FIGS. 10A and 10B are rear perspective views of the EEG headset module of the device of FIG. 1 showing both left and right reference electrodes adjusted along the axis when the device is worn.
Figure 10B:
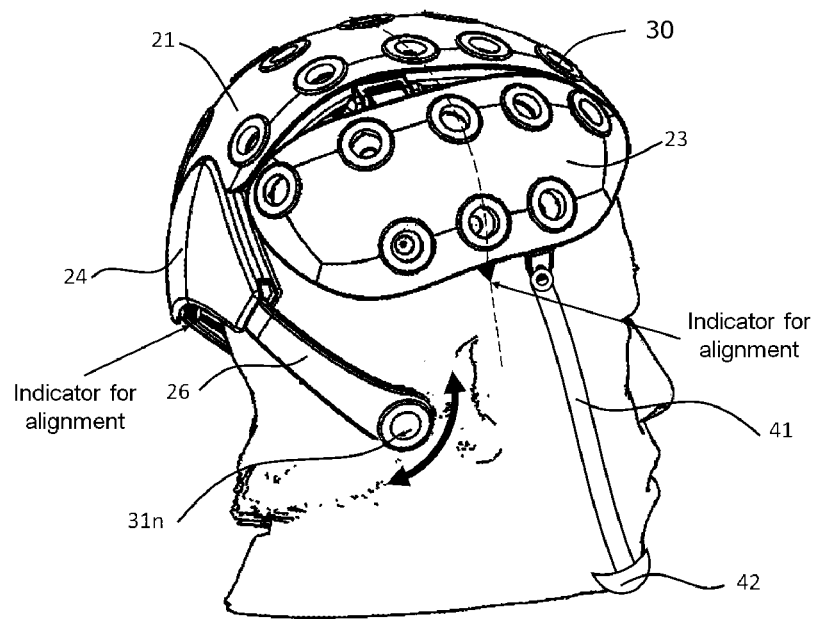

FIG. 10 depicts left reference electrode 25 and right reference electrode 26 that are located at the auxiliary segment 24 of the head-mountable device 181. The left reference electrode 25 and right reference electrode 26 can be adjusted along the axis at a selected angle to contact with the ear reference location.

Figure 11:
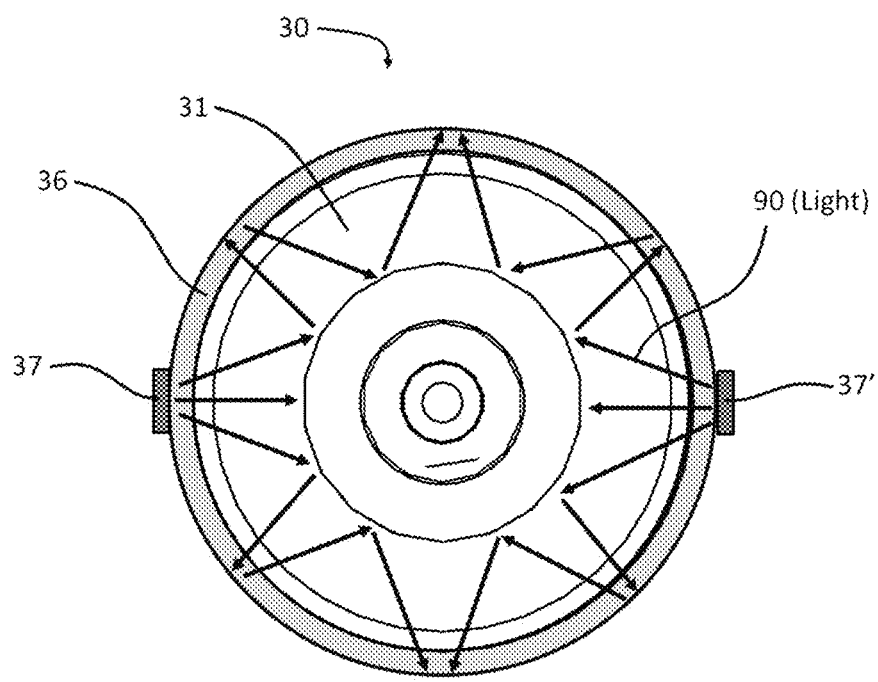
FIG. 11 is the top view of the self-orienting EEG electrode of FIG. 6 showing a diffused illumination pattern of the light ring for the visual bio-feedback signal.
Figure 12:
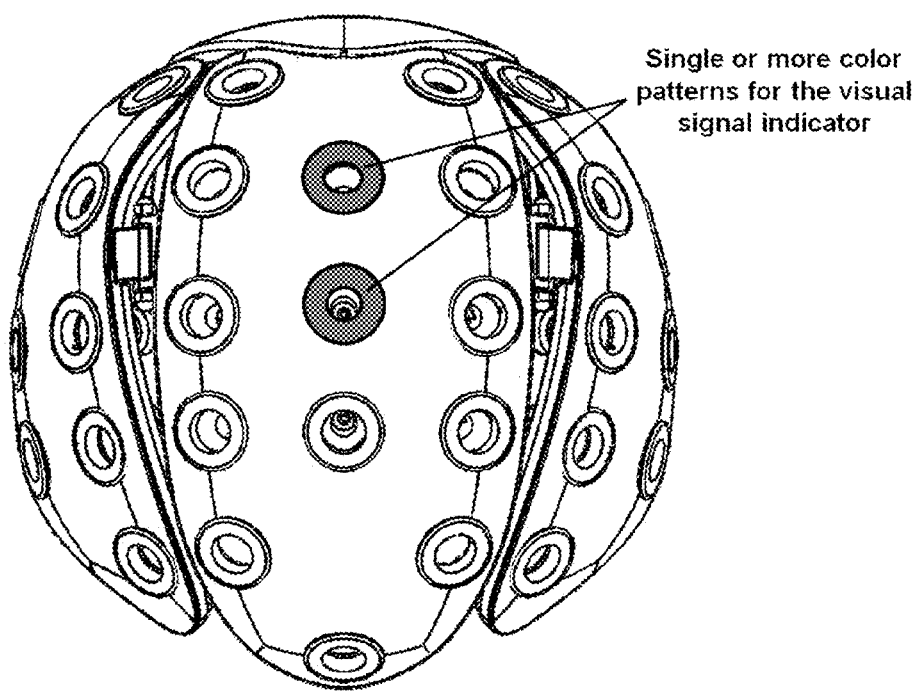
FIG. 12 is a top view of the EEG headset module of the device of FIG. 1 indicating the diffused illumination color pattern on the visual signal indicator of FIG. 11 which placed outside of the device.

Referring to FIG. 11 and FIG. 12, the visual bio-feedback signal indicators 37 are incorporated in the electrode design to diffuse a color pattern on the light ring 36 which is placed outside of the device. The visual signal indicators can show the skin-electrode impedance value, the EEG value, or control parameters. The visual signal indicator can be one or more LEDs 37 with single or more colors. The color patterns and intensity represent impedance, EEG value or control parameters. The color is not limited to cover only the above pattern and parameters.

In order to provide better signal-to-noise ratio for the EEG signals, a pre-amplifier 40 can be attached physically close to each electrode. The amplifier 40 can be arranged in a single unit or in the form of an array.

As set forth above, the present invention provides an improved biofeedback device that is portable, easy-to-use, and minimizes the preparation time for brain training both in a hospital and home setting. While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure. The disclosure of all cited references is incorporated by reference herein.

REFERENCES

1. R. Ball, C. Shu, P. C. Xi, M. Rioux, Y. Luximon, and J. Molenbroek, "A comparison between Chinese and Caucasian head shapes," Applied Ergonomics, vol. 41, pp. 832-839, 2010
2. Z. Zhuang, S. Benson, D. "Viscusi. Digital 3-D headforms with facial features representative of the current U.S. work force," Ergonomics; 53: 661-71,2010
3. China National Institute of Standardization. (1998) CNIS GB/T2428:1998. Head-face dimensions of adults by Xiao H, Hua D H, Yang T X, Zhang Z B, Bi G X, Liu J M.

Beijing, China: General Administration of Quality Supervision, Inspection and Quarantine of the People's Republic of China.
4. China National Institute of Standardization. (1998) CNIS GB/T2428:1998. Head-face dimensions of adults by Xiao H, Hua D H, Yang T X, Zhang Z B, Bi G X, Liu J M. Beijing, China: General Administration of Quality Supervision, Inspection and Quarantine of the People's Republic of China.
5. China National Institute of Standardization. (1981) CNIS GB2428-81. Head styles of adults by Beijing Institute of Labor Protection. Beijing, China: General Administration of Quality Supervision, Inspection and Quarantine of the People's Republic of China.
6. Y. Yu, S. Benson, W. Cheng, J. Hsiao, Y. Liu, Z. Zhuang and W. Chen. "Digital 3-D Headforms Representative of Chinese Workers" Ann. Occup. Hyg., pp. 1-10, 2011

The disclosure of the foregoing cited references is incorporated herein by reference.

What is claimed is:

1. A head-mountable device including an electrode array for measuring bioelectrical signals generated by a cerebral cortex of a brain configured such that individual electrodes are radially adjustable for individual variations in head size and shape comprising:
   a plurality of head-mountable device sections;
   a plurality of mechanical fasteners connecting the head-mountable device sections; wherein the head-mountable device sections can be bent upward and downward by the mechanical fasteners during application and removal of the device such that the device sections are moveable relative to one another;
   an array of resilient sleeves within each head-mountable device section, each sleeve housing an individual electrode, the resilient sleeve being deformable for self-orienting such that a central axis passing through the individual electrode housed within the resilient sleeve is maintained in a position approximately normal to a plane tangential to a scalp portion positioned beneath the electrode; and
   a damper portion integral of at least one of the resilient sleeves and configured to be deformable for maintaining the orientation of the individual electrode relative to the scalp portion beneath the individual electrode.

2. The head-mountable device according to claim 1 wherein the mechanical fasteners comprise one or more hinge joints.

3. The head-mountable device according to claim 1 wherein the damper portion is a semicircular damper portion.

4. The head-mountable device according to claim 1 further comprising a pre-amplifier adjacent to one or more of the individual electrodes in the electrode array.

5. The head-mountable device according to claim 4 wherein the pre-amplifier is a single unit or an array.

6. The head-mountable device according to claim 1 further comprising an auxiliary head-mountable segment including reference electrodes alignable with an ear reference location, wherein the auxiliary head-mountable segment is attached to at least one of the head-mountable device sections.

7. The head-mountable device according to claim 1 further comprising an annular groove positioned within the resilient sleeve for holding electrode legs.

* * * * *